(12) United States Patent
Weaver et al.

(10) Patent No.: US 6,623,486 B1
(45) Date of Patent: Sep. 23, 2003

(54) BONE PLATING SYSTEM

(75) Inventors: Paul C. Weaver, Douglassville, PA (US); Jeff W. Mast, Grosse Pointe Park, MI (US); Keith A. Mayo, Harrison Township, MI (US); Brett R. Bolhofner, St. Petersburg, FL (US); David Little, West Chester, PA (US)

(73) Assignee: Synthes (U.S.A.), Paoli, PA (US)

( * ) Notice: Subject to any disclaimer, the term of this patent is extended or adjusted under 35 U.S.C. 154(b) by 216 days.

(21) Appl. No.: 09/660,287

(22) Filed: Sep. 12, 2000

Related U.S. Application Data
(60) Provisional application No. 60/153,239, filed on Sep. 13, 1999.

(51) Int. Cl.[7] ............................................. A61B 17/56
(52) U.S. Cl. ............................................................ 606/69
(58) Field of Search ............................... 606/65, 69, 70, 606/71, 61

(56) References Cited

U.S. PATENT DOCUMENTS

| | | | |
|---|---|---|---|
| RE28,841 E | 6/1976 | Allgower et al. | |
| 4,408,601 A | 10/1983 | Wenk | |
| 4,565,193 A | 1/1986 | Streli | |
| 4,838,252 A | 6/1989 | Klaue | |
| 4,927,421 A | 5/1990 | Goble et al. | |
| 4,988,350 A | 1/1991 | Herzberg | |
| 5,002,544 A | 3/1991 | Klaue et al. | |
| 5,041,114 A | 8/1991 | Chapman et al. | |
| 5,085,660 A | 2/1992 | Lin | |
| 5,129,901 A | 7/1992 | Decoste | |
| 5,151,103 A | 9/1992 | Tepic et al. | |
| 5,190,544 A | 3/1993 | Chapman et al. | |
| 5,197,966 A | 3/1993 | Sommerkamp | |
| 5,269,784 A | 12/1993 | Mast | |
| 5,275,601 A | 1/1994 | Gogolewski et al. | |
| 5,304,180 A | 4/1994 | Slocum | |
| 5,324,290 A | 6/1994 | Zdeblick et al. | |
| 5,364,398 A | 11/1994 | Chapman et al. | |
| 5,364,399 A | * 11/1994 | Lowery et al. | ................ 606/69 |

(List continued on next page.)

FOREIGN PATENT DOCUMENTS

| | | |
|---|---|---|
| DE | 43 41 980 A1 | 6/1995 |
| DE | 43 43 117 A1 | 6/1995 |
| FR | 2233973 | 1/1975 |
| FR | 2405062 | 5/1979 |
| FR | 2405705 | 5/1979 |
| FR | 2405706 | 5/1979 |
| FR | 2496429 | 5/1979 |
| SU | 1279626 A1 | 12/1986 |
| WO | WO 97/09000 | 3/1997 |
| WO | WO 0053110 | 9/2000 |
| WO | WO 0053111 | 9/2000 |

\* cited by examiner

*Primary Examiner*—Eduardo C. Robert
(74) *Attorney, Agent, or Firm*—Pennie & Edmonds, LLP

(57) ABSTRACT

The present invention relates to a bone plating system and method for fracture fixation of bone. The bone plating system includes a bone plate, at least one locking screw, and at least one non-locking screw. The bone plate has locking holes with threads and non-locking holes. The locking screws have a shaft with a thread for engaging bone and a head with a thread configured and dimensioned to mate with the thread of the locking holes. The non-locking screws have a thread for engaging bone and a non-threaded head. Both the locking and non-locking screws remain seated in their respective holes for substantially as long as the bone plate is implanted. The non-locking screws compress the bone plate against the bone and hold fracture reduction while the locking screws are secured to the plate at a fixed angular relationship. The mixed fixation achieved by this bone plating system and method is particularly useful for treatment of per-articular fractures.

18 Claims, 9 Drawing Sheets

U.S. PATENT DOCUMENTS

| | | |
|---|---|---|
| 5,429,641 A | 7/1995 | Gotfried |
| 5,514,138 A * | 5/1996 | McCarthy .................... 606/65 |
| 5,591,168 A * | 1/1997 | Judet et al. .................... 606/65 |
| 5,601,553 A | 2/1997 | Trebing et al. |
| 5,709,686 A | 1/1998 | Talos et al. |
| 5,741,258 A | 4/1998 | Klaue et al. |
| 5,749,872 A | 5/1998 | Kyle et al. |
| 5,772,662 A | 6/1998 | Chapman et al. |
| 5,810,823 A | 9/1998 | Klaue et al. |
| 5,968,047 A * | 10/1999 | Reed ........................... 606/76 |
| 6,022,352 A * | 2/2000 | Vandewalle ................... 606/73 |
| 6,096,040 A | 8/2000 | Esser |
| 6,129,730 A * | 10/2000 | Bono et al. .................... 606/73 |
| 6,183,475 B1 * | 2/2001 | Lester et al. ................... 606/69 |
| 6,228,085 B1 * | 5/2001 | Theken et al. ................. 606/61 |

BONE PLATING SYSTEM

CROSS-REFERENCE TO RELATED APPLICATIONS

The benefit of Provisional Application No. 60/153,239 filed on Sep. 13, 1999 is claimed under 35 U.S.C. §119(e).

FIELD OF THE INVENTION

The present invention is directed to a bone plating system for fracture fixation, and in particular to a system including a bone plate having plate holes for both locking and non-locking screws.

BACKGROUND OF THE INVENTION

The clinical success of plate and screw systems for internal fixation of fractures is well-documented. However, treatment of certain fractures, such as peri-articular fractures, which require a fixed angular relationship between the bone plate and screws, remains problematic. Fixed angle devices for treatment of these fractures are available and include the Dynamic Condylar Screw System commercially available from Synthes (USA) of Paoli, PA and a wide variety of blade plates. All of these devices require a high level of surgical skill, suitable bone quantity and quality, and a fracture pattern compatible with the device.

In cases in which these requirements are not satisfied, e.g. severely comminuted bone or missing bone segments, conventional bone plate and screw systems must be used. Although these conventional systems are particularly well-suited to promoting healing of the fracture by compressing the fracture ends together and drawing the bone into close apposition with other fragments and the bone plate, the angular relationships between the plate and screws are not fixed and can change postoperatively. This can lead to malalignment and poor clinical results.

The primary mechanism for the change in angular relationship is related to energy storage. As previously noted, threading a bone screw into bone compresses the bone against the plate. The compression results in high strain in the bone, and, consequently, energy storage. With the dynamic loading resulting from physiological conditions, loosening of the plate and screw and loss of the stored energy can result.

Securing the screws to the plate provides a fixed angle relationship between the plate and screw and reduces the incidence of loosening. One method of securing the screw to the plate involves the use of so-called "locking screws." A locking screw has threading on an outer surface of its head that mates with corresponding threading on the surface of a plate hole to lock the screw to the plate. Bone plates having threaded holes for accommodating locking screws are known. For example, German Patent Application No. 43 43 117 discloses a bone plate with threaded holes for locking screws. As the relationship between the locking screws and the plate is fixed, locking screws provide a high resistance to shear or torsional forces. However, locking screws have a limited capability to compress bone fragments.

In summary, conventional bone screws, i.e. screws that are not secured to a plate so that a fixed angular relationship between the plate and screw is maintained (hereinafter "non-locking screws") effectively compress bone fragments, but possess a low resistance to shear force that can lead to loosening of the screw. Locking screws have a high resistance to shear force that ensure stability at the bone screw/plate hole interface, but possess a limited ability to compress bone fragments. Thus, a bone plating system that combines non-locking screws with locking screws would be ideal for certain clinical situations.

U.S. Patent No. 5,601,553 discloses a locking plate and bone screw. The plate has a plurality of threaded plate holes for receiving locking screws. The plate also has non-threaded plate holes for receiving temporary screws that keep the plate in place while the locking screws are inserted. After the locking screws are inserted, the temporary screws are removed. Thus, the long term benefits of combining non-locking screws with locking screws are not obtained. U.S. Pat. No. 5,709,686 discloses a bone plate with partially threaded plate holes. The partially threaded holes allow either non-locking or locking screws to be used. Because the plate holes are only partially threaded, the locking screws used may not be able to maintain the fixed angular relationship between the screws and plate under physiological loads. Specifically, the locking screws within the plate are only partially captivated and thus only partially surrounded by threads. Under high stress and loading conditions, the locking plate hole may distort and allow the fixed angular relationship between the locking screw and plate to change. This can result in loss of fixation or loss of established intraoperative plate orientation. Additionally, because of the plate hole geometry, translation of the plate with the non-locking screws is limited to one direction only. This may be a disadvantage in reduction and manipulation of fragments.

Thus, there exists a need for an improved bone plating system that overcomes the deficiencies of the prior art.

SUMMARY OF THE INVENTION

The bone plating system for fixation of bone according to the present invention includes a bone plate having an upper surface, a bone-contacting surface, at least one first hole passing through the upper and bone-contacting surfaces and having a thread, and at least one second hole passing through the upper and bone-contacting surfaces. The bone plating system also includes a first screw having a shaft with a thread for engaging bone and a head with a thread configured and dimensioned to mate with the thread of the first hole, and a second screw having a shaft with a thread for engaging bone and a head. The first and second screws remain seated in their respective holes for substantially as long as the bone plate is implanted. Preferably, the bone plate includes a plurality of first and second holes, and a corresponding plurality of first and second screws are provided.

In order to facilitate insertion, the first and second screws can be a self-tapping screws. These screws can also be self-drilling screws. Additionally, the first and second screws can be cannulated for insertion of a guide wire to guide screw placement. The first plate hole can have a substantially conical shape with a double-lead thread.

In one embodiment, the bone plate has a trapezoidal shaped cross section in regions between the first and second plate holes for minimizing contact between bone and the bone-contacting surface. Additionally, at least one of the second plate holes is longitudinally elongated and has an edge inclined at an angle to the upper surface toward the bone-contacting surface for displacing the bone plate when engaged by the head of a second bone screw.

In an exemplary embodiment, the vone plate includes a head portion configured and dimensioned to conform to a metaphysis of a bone and a shaft portion configured and dimensioned to conform to a diaphysis of a bone. The head portion has only first plate holes and the shaft portion has both first and second plate holes. In one embodiment, the head portion has a curved surface, includes an anterior fork substantially parallel to an anterior side of the shaft portion, and includes a posterior fork extending out from a posterior side of the shaft portion. In another embodiment, the head portion flares outward from the shaft portion and is curved, tapered, and twisted. The head portion can also be provided with suture holes from suture anchoring of the bone plate.

The method for fracture fixation of bone according to the present invention comprises the steps of reducing the fracture to bring bone fragments in close apposition; compressing a bone plate against the bone with at least one first fastener to hold the fracture reduction; and securing at least one second fastener at a fixed angular relationship to the bone plate. The first fasteners are inserted before the second fasteners and both the first and second fasteners remain in bone for substantially as long as the bone plate is implanted.

DESCRIPTION OF THE PREFERRED EMBODIMENTS

Figure 1:
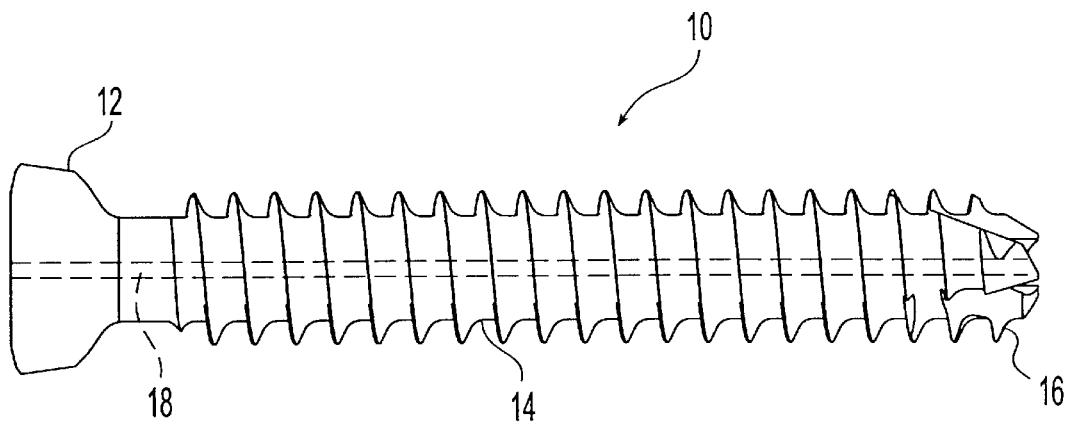
FIG. 1 is a side view of one embodiment of a non-locking screw according to the present invention.

The bone plating system according to the present invention includes a bone plate, non-locking screws, and locking screws. FIG. 1 shows an example of a non-locking screw 10 that can be used with the present invention. In general and as described in more detail below, any surgical screw that has a non-threaded head 12 of an appropriate size and geometry for select plate holes of the bone plate can be used. Non-locking screw 10 has a shaft 14 that is at least partially threaded for attachment to bone. The length of shaft 14 and the shaft thread configuration can be selected for the particular application. As is well known in the art, the threads and a tip 16 can be made to be self-tapping and/or self-drilling to facilitate implantation. Shaft 14 can also be cannulated with a channel for receiving a guide wire to aid in proper placement.

Figure 2:
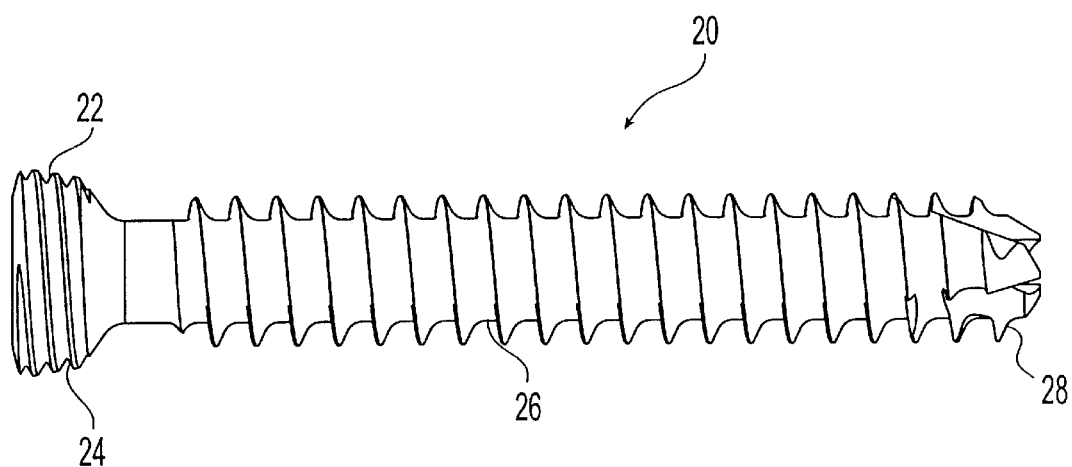
FIG. 2 is a side view of one embodiment of a locking screw according to the present invention.

FIG. 2 shows an example of a locking screw 20 that can be used with the present invention. In general and as described in more detail below, any surgical screw that has a head 22 with threads 24 can be used as long as head 22 is of an appropriate size and geometry for select plate holes of the bone plate and threads 24 mate with the threads of the plate holes. Locking screw 20 has a shaft 26 that is at least partially threaded for attachment to bone. The length of shaft 26 and the shaft thread configuration can be selected for the particular application. As is well known in the art, the threads and a tip 28 can be made to be self-tapping and/or self-drilling to facilitate implantation. Shaft 26 can be cannulated for receiving a guide wire.

Figure 3:
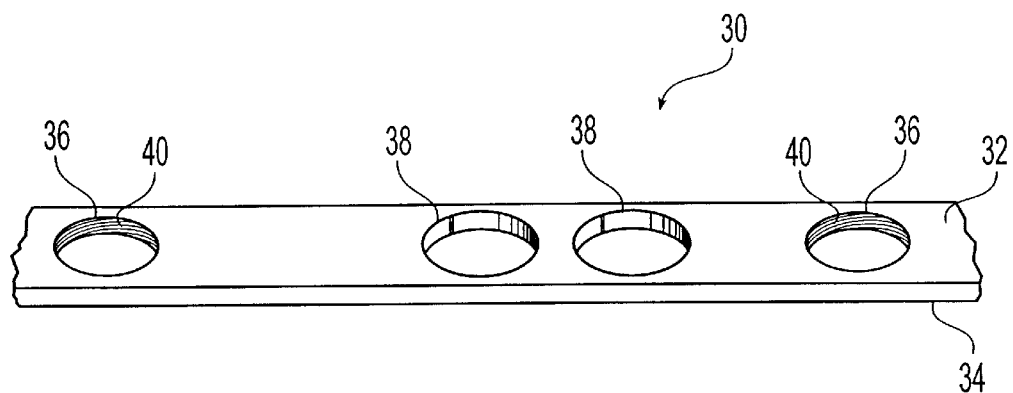
FIG. 3 is a perspective view of a portion of a bone plate according to the present invention.
Figure 9:
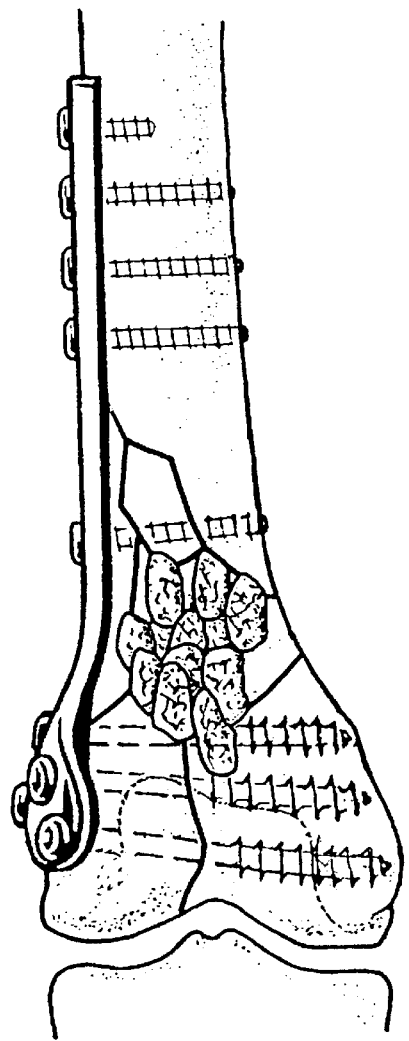
FIG. 9 shows a perspective view of the bone plate of FIG. 7 implanted in a distal femur.

FIG. 3 shows a portion of a bone plate 30 according to the present invention. Bone plate 30 can be made in different shapes and sizes for use in a wide variety of clinical applications. Bone plate 30 includes an upper surface 32 and a bone contacting surface 34. Bone plate 30 has a plurality of first plate holes 36 and a plurality of second plate holes 38. Each of first and second plate holes 36, 38 passes through upper 32 and bone-contacting surfaces 34. Each first plate hole 36 has a thread 40 that mates with thread 24 on head 22 of locking screw 20 to secure locking screw 20 to bone plate 30 at a temporally fixed angular orientation. Second plate holes 38 are not threaded and receive non-locking screws 10 with non-threaded heads 12. Insertion of non-locking screws 10 in second plate holes 38 draws the bone toward bone-contacting surface 34 to compress the bone. Thus, seating of non-locking screws 10 in second plate holes 38 compresses the bone against bone-contacting surface 34 and seating of locking screws 20 in first plate holes 36 secures heads 22 to bone plate 30 for maintaining a fixed angular relationship between locking screws 20 and bone plate 30. Simultaneous use of bone plate 30 with both non-locking and locking screws 10, 20 for as long as bone plate 30 is implanted provides stability between both the screw and bone plate and between the bone plate and bone. As non-locking screws 10 are generally secured in cancellous bone, the threads on shaft 14 are typically larger than the threads on shaft 26 of locking screws 20.

Figure 4:
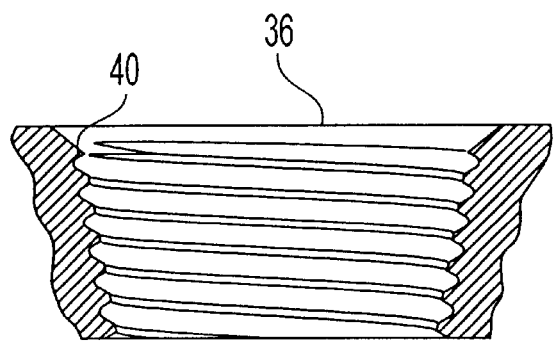
FIG. 4 shows a cross-sectional view of one of the first plate holes through line 4—4 of FIG. 3.

First plate holes 36 are preferably conical in shape. As shown in FIG. 4, threads 40 on first plate holes 36 are also preferably double lead threads. The double lead conical threads enables multiple threads to engage while maintaining a low profile. Additionally, the double lead conical threads are less susceptible to cross-threading compared to other threads, e.g. cylindrical threaded arrangements.

Figure 5:
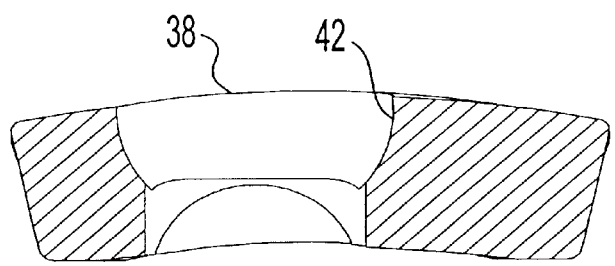
FIG. 5 shows a cross-sectional view of one of the second plate holes through line 5—5 of FIG. 3.
Figure 6:
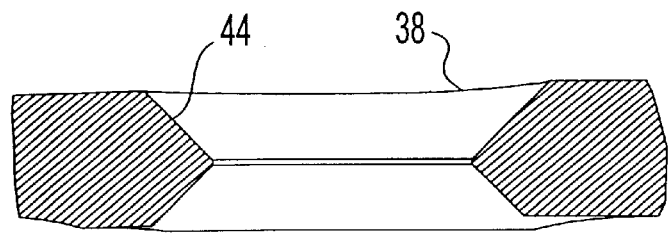
FIG. 6 shows another cross-sectional view of the second plate hole of FIG. 5 through line 6—6 of FIG. 3.
Figure 7:
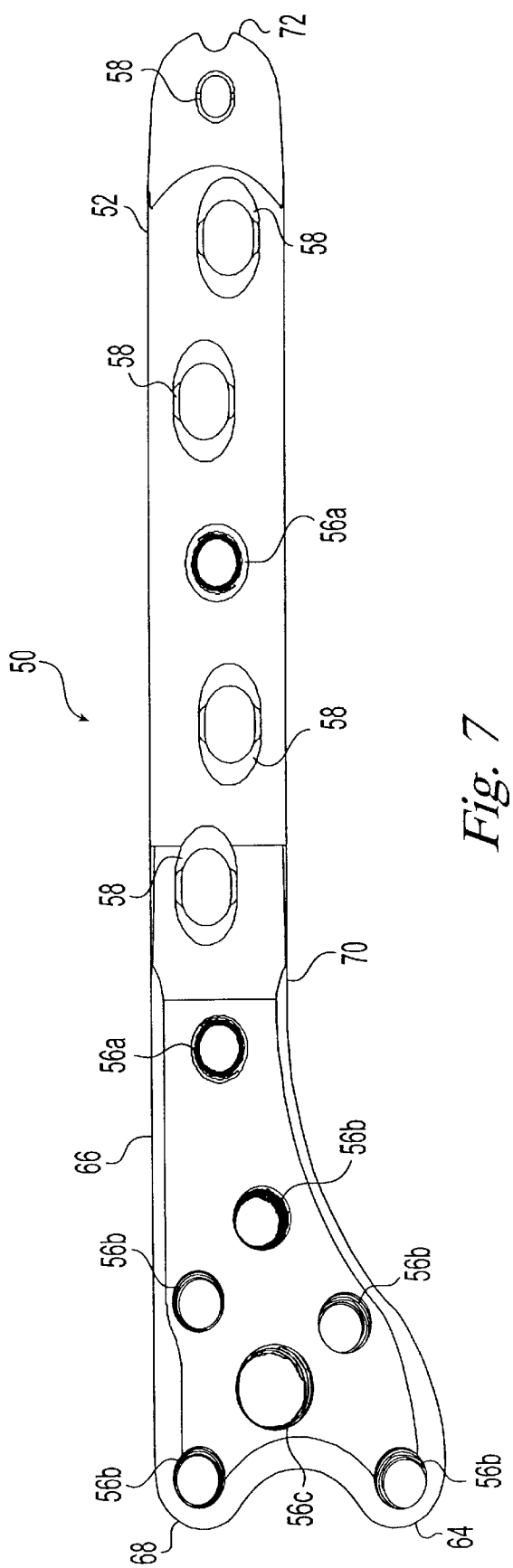
FIG. 7 shows a top view of an embodiment of a bone plate according to the present invention designed for use in the distal femur.

As seen best in FIGS. 5 and 6, second plate holes 38 are preferably dynamic compression unit (DCU) screw holes substantially similar to those disclosed in reissued U.S. Patent No. Re. 31,628 to Allgower et al., the contents of which are incorporated herein by reference. The DCU screw holes promote healing of the bone by compressing the fracture ends together. Briefly, second plate holes 38 have an edge 42 which includes an oblique portion or ramp 44 having an inclination such that when ramp 44 is engaged by the underside of head 12 of non-locking screw 10, bone plate 30 is displaced in a direction to move ramp 44 away from non-locking screw 10 and to cause bone plate 30 to apply a pressure to hold the fracture ends in tight engagement.

Bone-contacting surface 34 on bone plate 30 can be shaped to minimize contact with bone. Limiting contact between the bone plate and bone has a number of biological and mechanical advantages including reduced damage to blood supply and easier plate removal. Providing bone plate 30 with a trapezoidal cross section (FIG. 11) in the regions between a first and second plate holes 34, 36 is one way to minimize contact. Other ways are disclosed in U.S. Pat. Nos. 5,151,103; 5,053,036; 5,002,544; and 4,838,252. The contents of these patents are incorporated herein by reference.

By combining locking screws and non-locking screws on the same bone plate, the present invention provides a novel mixed fixation. With the non-locking screws, fracture reduction is held by friction between the bone plate and bone. This friction is generated by tightening the non-locking screws in bone. However, micromotion between the non-locking screws and bone leads to bone resorption, and loss of reduction. Additionally, insertion of the non-locking screws requires bone to withstand the stresses of tightening of the screws. This results in high stress in bone surrounding the non-locking screws. Ordinarily, the high stress can cause the non-locking screw threads to strip (threads in bone fail in shear) and/or creep in bone (since bone is a viscoelastic material). Either one of these phenomenon also results in loss of reduction.

By adding at least one locking screw, loss of reduction is minimized or eliminated by the present invention. Specifically, by securing the locking screws to the bone plate and not the bone, the effect of the viscoelastic behavior of bone is reduced, the threads do not strip, and micromotion is prevented. The attachment between the locking screws and bone plate is a high strength connection in which the locking screw must cut sideways through bone to fail.

As management of certain peri-articular fractures typically involves insertion of screws at various angles with respect to the bone plate and it is highly desirable to maintain the initial angular relationships between the individual screws and the bone plate, the bone plating system according to the present invention is particularly well-suited for these clinical applications. FIGS. 7–19 show a bone plate 50 according to the present invention specifically designed for use in the distal femur. Bone plate 50 would be used primarily for, but not limited to, severely comminuted fractures including Hoffa type fractures.

Bone plate 50 has an upper surface 52 and a bone-contacting surface 54. Bone plate 50 has a plurality of threaded plate holes 56a, 56b, 56c (collectively referred to as threaded plate holes 56) for receiving locking screws 20 and a plurality of non-threaded plate holes 58 for receiving non-locking screws 10. Each of threaded and non-threaded plate holes 56, 58 passes through upper 52 and bone-contacting surfaces 54. As was the case for bone plate 30, the thread on threaded plate holes 56 mates with threaded head 22 of locking screw 20 to secure locking screw 20 to bone plate 50 at a temporally fixed angular orientation and insertion of non-locking screws 10 in non-threaded plate holes 58 draws the bone toward bone-contacting surface 54 to compress the bone.

Figure 8:
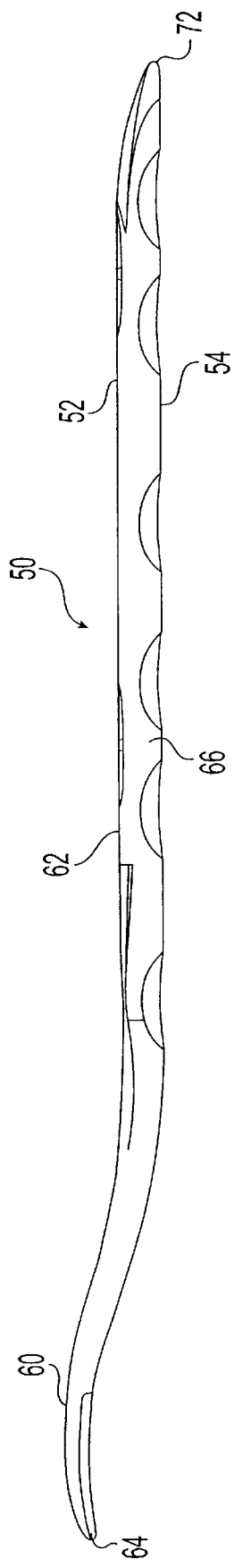
FIG. 8 shows a side view of the bone plate of FIG. 7.
Figure 10:
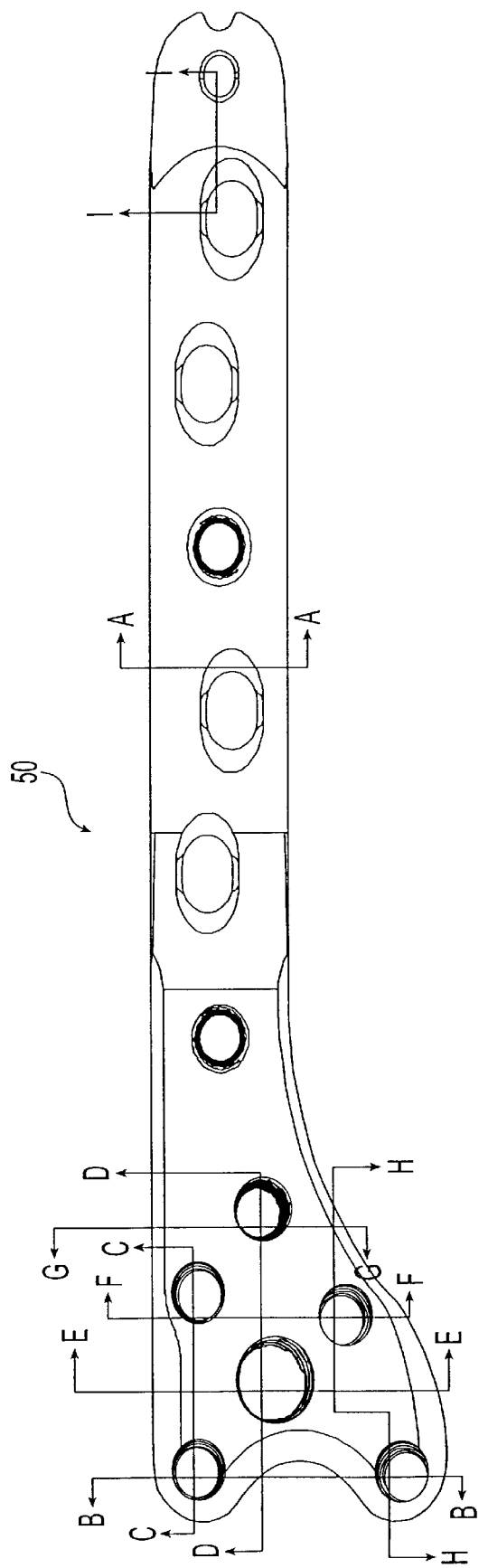
FIG. 10 shows a top view of the bone plate of FIG. 7 with various cross sections labeled.

Bone plate 50 includes a head portion 60 configured and dimensioned to conform to the metaphysis of the distal femur and a shaft portion 62 configured and dimensioned to conform to a diaphysis of a bone. As best seen in FIG. 8, bone contacting surface 54 of head portion 60 is a curved surface to fit the contours of the distal femur. Head portion 60 includes an anterior fork 64 substantially parallel to an anterior side 66 of shaft portion 62 and a posterior fork 68 extending laterally out from a posterior side 70 of shaft portion 62.

Figure 11:
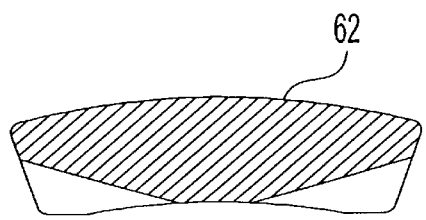
FIG. 11 shows a cross-section of the bone plate of FIG. 7 through line A—A.
Figure 12:
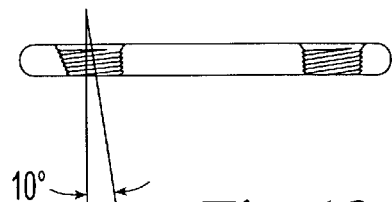
FIG. 12 shows a cross-section of the bone plate of FIG. 7 through line B—B.
Figure 13:
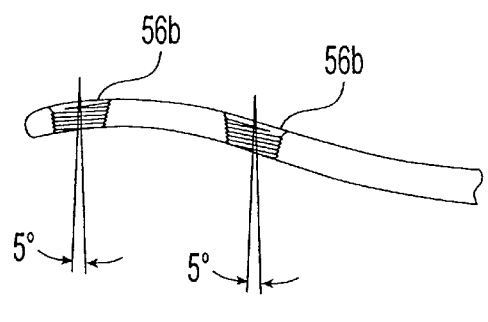
FIG. 13 shows a cross-section of the bone plate of FIG. 7 through line C—C.
Figure 14:
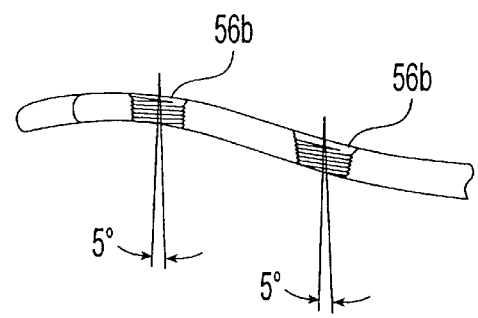
FIG. 14 shows a cross-section of the bone plate of FIG. 7 through line D—D.
Figure 15:
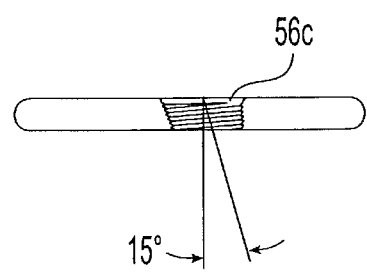
FIG. 15 shows a cross-section of the bone plate of FIG. 7 through line E—E.
Figure 16:
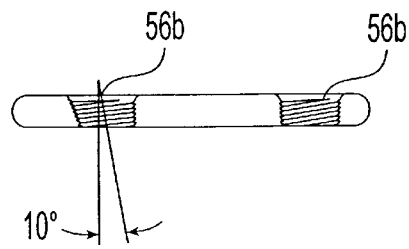
FIG. 16 shows a cross-section of the bone plate of FIG. 7 through line F—F.
Figure 17:
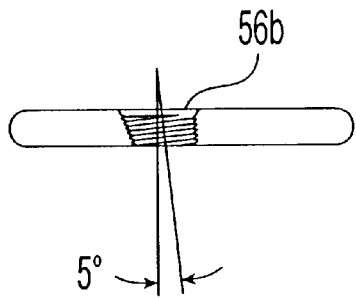
FIG. 17 shows a cross-section of the bone plate of FIG. 7 through line G—G.
Figure 18:
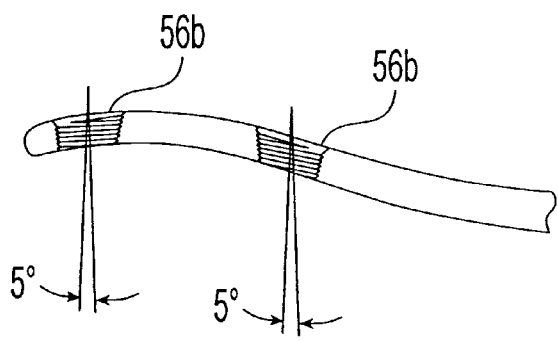
FIG. 18 shows a cross-section of the bone plate of FIG. 7 through line H—H.
Figure 19:
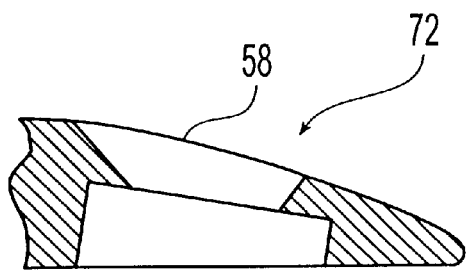
FIG. 19 shows a cross-section of the bone plate of FIG. 7 through line I—I

The non-threaded plate holes 58 are preferably dynamic compression unit (DCU) screw holes substantially similar to second plate holes 38. Shaft portion 62 has both threaded plate holes 56a and non-threaded plate holes 58 so that both locking and non-locking screws can be used in shaft portion 62. The ability to use locking screws in shaft portion 62 is particularly useful when the far cortex of part of the diaphysis is missing or severely damaged since fixation with non-locking screws is problematic because of the condition of the far cortex. As best seen in FIG. 11, the regions between threaded and nonthreaded plate holes 56a, 58 have a trapezoidal cross section that limits contact between bone-contacting surface 54 of shaft portion 62 and the femur. Shaft portion 62 terminates in a tapered tail 72 (FIG. 19).

In contrast to shaft portion 62, head portion 60 contains only threaded holes 56. Specifically, threaded plate holes 56b that surround a centrally located threaded plate hole 56c. Threaded plate hole 56c has a larger diameter than threaded plate holes 56b to accommodate a locking screw with a larger diameter, e.g. threaded plate hole 56b have a diameter of 5.0 mm and threaded plate hole 56c has a diameter of 7.3 mm. FIGS. 12–18 show the various angular orientations of the individual threaded holes 56b, 56c. In generally, threaded holes 56b, 56c are arranged so that the inserted locking screws converge towards each other. It should be noted that, if a surgeon elects, non-locking screws can be used in any of threaded plate holes 56. Finally, it should also be noted that bone plate 50 has several structural differences from the condylar buttress plate commercially available from Synthes (U.S.A.) of Paoli, Pa. For example, the head of the condylar buttress plate is contoured in both the longitudinal and transverse directions while head portion 60 of bone plate 50 is contoured only in the longitudinal direction for a more anatomical fit. Additionally, tail 72 has an elevated end to get under tissue.

FIGS. 20–26 show a bone plate 80 according to the present invention specifically designed for use in the proximal tibia. Bone plate 80 would be primarily used for, but not limited to fractures of the lateral proximal tibial plateau. Bone plate 80 has an upper surface 82 and a bone-contacting surface 84. Bone plate 80 has a plurality of threaded plate holes 86a, 86b and 86c (collectively referred to as threaded plate holes 86) for receiving locking screws 20 and a plurality of non-threaded plate holes 88 for receiving non-locking screws 10. Each of threaded and non-threaded plate holes 86 and 88 pass through upper 82 and bone-contacting surfaces 84. As was the case for bone plate 30, the threads on threaded plate holes 86 mate with the threaded head 22 of locking screw 20 to secure locking screw 20 to bone plate 80 at a fixed angular orientation. Insertion of non-locking screws 10 in non-threaded plate holes 88 draws the bone-contacting surface 84 toward the bone to compress the plate to the bone.

Figure 20:
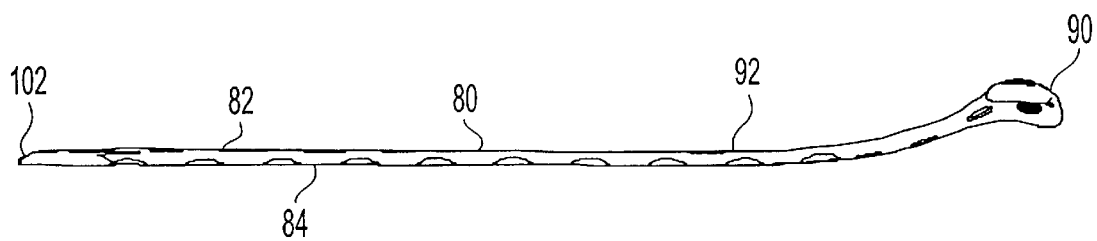
FIG. 20 shows a side view of an embodiment of a bone plate according to the present invention designed for use in the proximal tibia.
Figure 21:
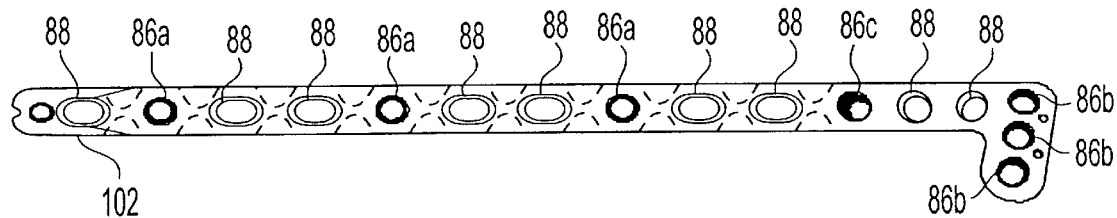
FIG. 21 shows a top view of the bone plate of FIG. 20.
Figure 22:
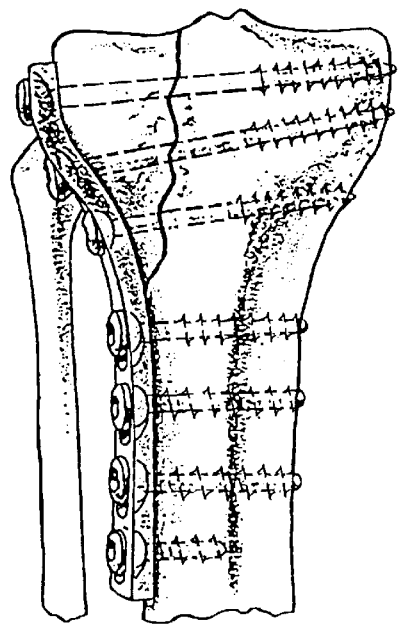
FIG. 22 shows a perspective view of the bone plate of FIG. 20 implanted in a proximal tibia.
Figure 26:
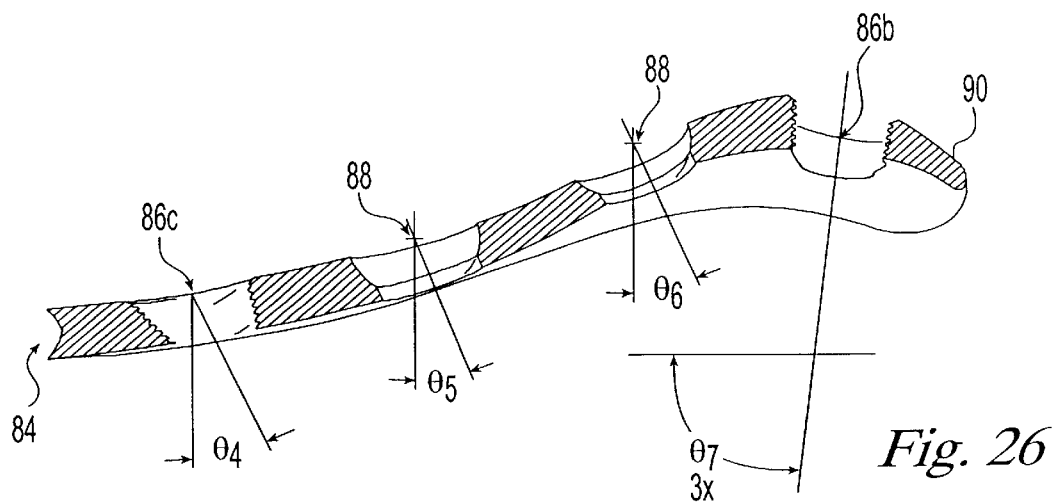
FIG. 26 shows a cross-section of the bone plate of FIG. 21 through line D—D.

Bone plate 80 includes a head portion 90 configured and dimensioned to conform to the metaphysis of the lateral proximal tibia and a shaft portion 92 configured and dimensioned to conform to a diaphysis of the lateral proximal tibia. As seen in FIGS. 20 and 26, bone contacting surface 84 of head portion 90 is a curved, tapered, and twisted to fit the contours of the lateral proximal tibial plateau. Head portion 90 also features sutures holes for suture anchoring and for provisional fixation of bone plate 80.

Figure 24:
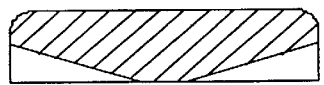
FIG. 24 shows a cross-section of the bone plate of FIG. 21 through line A—A.
Figure 25:
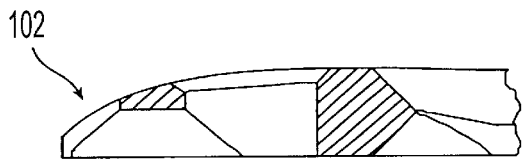
FIG. 25 shows a cross-section of the bone plate of FIG. 21 through line I—I.

The non-threaded plate holes 88 are preferably dynamic compression unit (DCU) screw holes substantially similar to second plate holes 38. Shaft portion 92 has both threaded plate holes 86*a* and non-threaded plate holes 88 so that both locking and non-locking screws can be used in shaft portion 92. The ability to use locking screws in shaft portion 92 is particularly useful when the far cortex of part of the diaphysis is missing or severely damaged since fixation with non-locking screws is problematic because of the condition of the far cortex. As best seen in FIG. 24, the regions between threaded and nonthreaded plate holes 86*a* and 88 have a rectangular cross section that limits contact between bone-contacting surface 84 of shaft portion 92 and the tibia. Shaft portion 92 terminates in a tapered tail 102 (FIG. 25).

Figure 23:
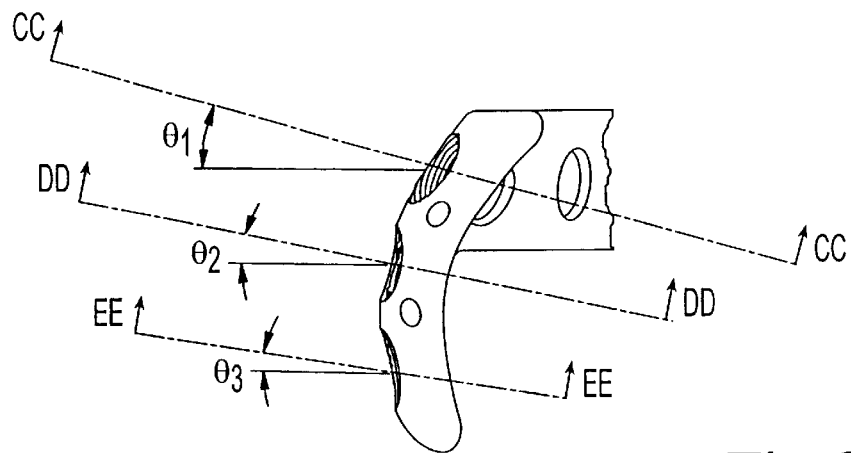
FIG. 23 shows an end view of the bone plate of FIG. 20 with various cross sections labeled.

In similar fashion to shaft portion 92, head portion 90 contains threaded holes 86 and non-threaded holes 88. Head portion 90 features threaded plate holes 86*b* and 86*c*. Holes 86*b* and 86*c* have a diameter of 5.0 mm and are oriented as shown in FIGS. 23 and 26. In general, threaded holes 86*b*, 86*c* are arranged so that the inserted locking screws converge towards each other. As shown in FIG. 23, plate holes 86*b* are oriented to converge at a predetermined distance from plate surface 84 to optimize the position of locking screws 20 within the tibia plateau. As shown in FIG. 26, plate hole 86*c* is oriented to converge with plate hole 86*b* at predetermined distance to provide additional stability to the locked fixed-angle construct. It should be noted that if a surgeon elects, non-locking screws can be used in any of threaded plate holes 86.

While it is apparent that the illustrative embodiments of the invention herein disclosed fulfil the objectives stated above, it will be appreciated that numerous modifications and other embodiments may be devised by those skilled in the art. For example, for some fractures only one first plate hole and one second plate hole are needed, although at least two of each is advantageous. Furthermore, additional plate holes without screws can be present in the plate, if desired to allow the surgeon further flexibility in use. Therefore, it will be understood that the appended claims are intended to cover all such modifications and embodiments which come within the spirit and scope of the present invention.

What is claimed is:

1. A bone plating system for fixation of bone comprising:
 a bone plate having:
  an upper surface;
  a bone-contacting surface;
  at least one first hole passing through the upper and bone-contacting surfaces and having a thread; and
  at least one second hole passing through the upper and bone-contacting surfaces;
 a first screw having a shaft with a thread for engaging bone and a head with a thread configured and dimensioned to mate with the thread of the first hole; and
 a second screw having a shaft with a thread for engaging bone and a head, wherein the first and second screws remain seated in their respective holes for substantially as long as the bone plate is implanted,
 wherein the bone plate includes a plurality of first and second holes, and a corresponding plurality of first and second screws are provided, and
 wherein the bone plate includes a head portion configured and dimensioned to conform to a metaphysis of a bone and a shaft portion configured and dimensioned to conform to a diaphysis of a bone and the head portion has only first plate holes.

2. The bone plating system of claim 1 wherein the first screw is a self-tapping screw.

3. The bone plating system of claim 1 wherein the first screw is a self-drilling screw.

4. The bone plating system of claim 1 wherein the first screw is cannulated for insertion of a guide wire to guide screw placement.

5. The bone plating system of claim 1 wherein the second screw is a self-tapping screw.

6. The bone plating system of claim 1 wherein the first plate hole substantially conical shape.

7. The bone plating system of claim 6 wherein the first plate hole has a double-lead thread.

8. The bone plating system of claim 1 wherein the bone plate has a trapezoidal shaped cross section in regions between the first and second plate holes for minimizing contact between bone and the bone-contacting surface.

9. The bone plating system of claim 1 wherein at least one of the second plate holes is longitudinally elongated and has an edge inclined at an angle to the upper surface toward the bone-contacting surface for displacing the bone plate when engaged by the head of a second bone screw.

10. A method for fracture fixation of bone comprising the steps of:
 reducing the fracture to bring bone fragments in close apposition;
 compressing a bone plate against the bone with at least one first fastener to hold the fracture reduction; and
 securing at least one second fastener at a fixed angular relationship to the bone plate, wherein the at least one first fastener is inserted before the at least one second fastener and the at least one first fastener and the at least one second fastener remain in bone for substantially as long as the bone plate is implanted.

11. The method of claim 10, wherein the fracture is a peri-articular fracture.

12. The method of claim 10, wherein the fracture is adjacent at least one of the following group: a distal tibia, a proximal tibia, a distal femur, or proximal femur.

13. The method of claim 10, further comprising securing at least one third fastener at a fixed angular relationship to the bone plate, wherein third fastener is fixed at a different angular relationship to the bone plate than the second fastener.

14. A bone plating system for fixation of bone comprising:
 a bone plate having:
  an upper surface;
  a bone-contacting surface;
  at least one first hole passing through the upper and bone-contacting surfaces and having a thread; and
  at least one second hole passing through the upper and bone-contacting surfaces;

a first screw having a shaft with a thread for engaging bone and a head with a thread configured and dimensioned to mate with the thread of the first hole; and a second screw having a shaft with a thread for engaging bone and a head, wherein the first and second screws remain seated in their respective holes for substantially as long as the bone plate is implanted, wherein the bone plate includes a plurality of first and second holes, and a corresponding plurality of first and second screws are provided, and wherein the bone plate includes a head portion configured and dimensioned to conform to a metaphysis of a bone and a shaft portion configured and dimensioned to conform to a diaphysis of a bone and wherein the head portion flares outward from the shaft.

15. The bone plating system of claim 14 wherein the head portion is provided with suture holes.

16. A bone plating system for fixation of bone comprising:
a bone plate having:
an upper surface;
a bone-contacting surface;
at least one first hole passing through the upper and bone-contacting surfaces and having a thread; and
at least one second hole passing through the upper and bone-contacting surfaces;

a first screw having a shaft with a thread for engaging bone and a head with a thread configured and dimensioned to mate with the thread of the first hole; and a second screw having a shaft with a thread for engaging bone and a head, wherein the first and second screws remain seated in their respective holes for substantially as long as the bone plate is implanted, wherein the bone plate includes a plurality of first and second holes, and a corresponding plurality of first and second screws are provided, and wherein the bone plate includes a head portion configured and dimensioned to conform to a metaphysis of a bone and a shaft portion configured and dimensioned to conform to a diaphysis of a bone and wherein the head portion has a curved surface, includes an anterior fork substantially parallel to an anterior side of the shaft portion, and includes a posterior fork extending out from a posterior side of the shaft portion.

17. A bone plating system for fixation of bone comprising:
bone plate having:
an upper surface;
a bone-contacting surface;
at least one first hole passing through the upper and bone-contacting surfaces and having a thread; and
at least one second hole passing through the upper and bone-contacting surfaces;

a first screw having a shaft with a thread for engaging bone and a head with a thread configured and dimensioned to mate with the thread of the first hole; and a second screw having a shaft with a thread for engaging bone and a head, wherein the first and second screws remain seated in their respective holes for substantially as long as the bone plate is implanted, wherein the bone plate includes a plurality of first and second holes, and a corresponding plurality of first and second screws are provided, and wherein the bone plate includes a head portion configured and dimensioned to conform to a metaphysis of a bone and a shaft portion configured and dimensioned to conform to a diaphysis of a bone and wherein the shaft portion has both first and second plate holes.

18. A bone plating system for fixation of bone comprising:
a bone plate having:
an upper surface;
a bone-contacting surface;
at least one first hole passing through the upper and bone-contacting surfaces and having a thread; and
at least one second hole passing through the upper and bone-contacting surfaces;

a first screw having a shaft with a thread for engaging bone and a head with a thread configured and dimensioned to mate with the thread of the first hole; and a second screw having a shaft with a thread for engaging bone and a head, wherein the first and second screws remain seated in their respective holes for substantially as long as the bone plate is implanted, wherein the bone plate includes a plurality of first and second holes, and a corresponding plurality of first and second screws are provided, and wherein the bone plate includes a head portion configured and dimensioned to conform to a metaphysis of a bone and a shaft portion configured and dimensioned to conform to a diaphysis of a bone and wherein the shaft portion has a trapezoidal shaped cross section in regions between the first and second screw holes for minimizing contact between bone and the bone-contacting surface.

* * * * *

INTER PARTES REEXAMINATION CERTIFICATE (1133rd)
United States Patent
Weaver et al.

(10) Number: US 6,623,486 C1
(45) Certificate Issued: Jun. 23, 2015

(54) BONE PLATING SYSTEM

(75) Inventors: Paul C. Weaver, Douglassville, PA (US); Jeff W. Mast, Grosse Pointe Park, MI (US); Keith A. Mayo, Harrison Township, MI (US); Brett R. Bolhofner, St. Petersburg, FL (US); David Little, West Chester, PA (US)

(73) Assignee: SYNTHES USA, LLC, West Chester, PA (US)

Reexamination Request:
No. 95/000,468, May 8, 2009

No. 90/009,378, Jan. 8, 2009

Reexamination Certificate for:
Patent No.: 6,623,486
Issued: Sep. 23, 2003
Appl. No.: 09/660,287
Filed: Sep. 12, 2000

Related U.S. Application Data

(60) Provisional application No. 60/153,239, filed on Sep. 13, 1999.

(51) Int. Cl.
*A61B 17/80* (2006.01)
*A61B 17/68* (2006.01)

(52) U.S. Cl.
CPC ............. *A61B 17/80* (2013.01); *A61B 17/8057* (2013.01)

(58) Field of Classification Search
None
See application file for complete search history.

(56) References Cited

To view the complete listing of prior art documents cited during the proceedings for Reexamination Control Numbers 95/000,468 and 90/009,378, please refer to the USPTO's public Patent Application Information Retrieval (PAIR) system under the Display References tab.

*Primary Examiner* — David O Reip

(57) ABSTRACT

The present invention relates to a bone plating system and method for fracture fixation of bone. The bone plating system includes a bone plate, at least one locking screw, and at least one non-locking screw. The bone plate has locking holes with threads and non-locking holes. The locking screws have a shaft with a thread for engaging bone and a head with a thread configured and dimensioned to mate with the thread of the locking holes. The non-locking screws have a thread for engaging bone and a non-threaded head. Both the locking and non-locking screws remain seated in their respective holes for substantially as long as the bone plate is implanted. The non-locking screws compress the bone plate against the bone and hold fracture reduction while the locking screws are secured to the plate at a fixed angular relationship. The mixed fixation achieved by this bone plating system and method is particularly useful for treatment of per-articular fractures.

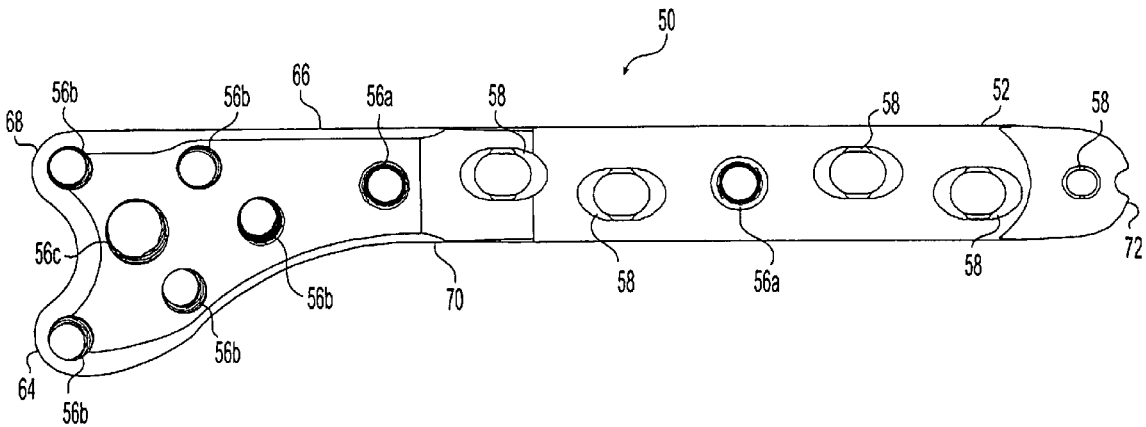

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-18 are cancelled.

\* \* \* \* \*